US 6,719,715 B2

(12) United States Patent
Newman et al.

(10) Patent No.: US 6,719,715 B2
(45) Date of Patent: Apr. 13, 2004

(54) APPARATUS AND PROCESS FOR CONDITIONING ORGANIC FLUID

(75) Inventors: Duncan Arthur Newman, Toronto (CA); Paul George Andrew Moore, Burlington (CA); Taras Worona, Etobicoke (CA); Jeffrey George Dayman, Waterloo (CA)

(73) Assignee: Vasogen Ireland Limited, County Clare (IE)

( * ) Notice: Subject to any disclaimer, the term of this patent is extended or adjusted under 35 U.S.C. 154(b) by 0 days.

(21) Appl. No.: 09/811,314

(22) Filed: Mar. 16, 2001

(65) Prior Publication Data

US 2003/0208105 A1 Nov. 6, 2003

Related U.S. Application Data

(60) Provisional application No. 60/154,215, filed on Sep. 16, 1999.

(51) Int. Cl.[7] ............................................. A61M 37/00
(52) U.S. Cl. ...................................... 604/6.08; 604/250
(58) Field of Search ............................. 604/6.08, 5.01, 604/250, 34; 210/195.2

(56) References Cited

U.S. PATENT DOCUMENTS

| 3,825,002 | A |   | 7/1974  | Paige       |          |
|-----------|---|---|---------|-------------|----------|
| 3,931,815 | A |   | 1/1976  | Takatsuki   |          |
| 4,321,919 | A | * | 3/1982  | Edelson     | 604/6.08 |
| 4,443,215 | A | * | 4/1984  | Smith       | 604/29   |
| 4,568,328 | A | * | 2/1986  | King        | 604/6.08 |
| 4,683,889 | A | * | 8/1987  | Edelson     | 607/92   |
| 5,209,800 | A |   | 5/1993  | Spencer et al. |       |
| 5,215,519 | A |   | 6/1993  | Shettigar   |          |
| 5,263,925 | A | * | 11/1993 | Gilmore et al. | 604/6.08 |
| 5,304,113 | A | * | 4/1994  | Sieber et al. | 604/6.08 |
| 5,951,509 | A | * | 9/1999  | Morris      | 604/6.08 |
| 6,193,681 | B1 | * | 2/2001 | Davidner et al. | 604/6.08 |

FOREIGN PATENT DOCUMENTS

| EP | 0 645 156 A   | 3/1995 |
| EP | 0 733 378 A2  | 9/1996 |
| WO | WO 01/19318 A1 | 3/2001 |

* cited by examiner

*Primary Examiner*—Alfred Basichas
(74) *Attorney, Agent, or Firm*—Burns, Doane, Swecker & Mathis, LLP (57) ABSTRACT

The invention provides apparatus for conditioning organic fluid for subsequent use in a medical procedure. The apparatus includes a cabinet having a secure environment and a door providing the only access to the environment. An input system is provided for transporting a organic fluid charge from a source to the cabinet and a container is removably contained in the secure environment and coupled to the charge input system to receive the charge. Stressors are coupled to the cabinet and positioned for operation to create a conditioned charge in the container An output system is coupled to the container and includes a receiver for the conditioned charge. The apparatus also includes a needle hub wherein a first end of the needle may be inserted intramuscularly while a second end of the needle projects beyond the patient's tissue and the second end being shielded. The apparatus also includes a heat sealing device for a thermoplastic medical tubing, thereby providing a sealed and closed batch system for treatment of the charge and thus reducing the risk of contamination of the charge, reducing the risk of cross contamination between charges, and reducing the risk of the charge contacting the operator.

21 Claims, 7 Drawing Sheets

APPARATUS AND PROCESS FOR CONDITIONING ORGANIC FLUID

CLAIM OF PRIORITY

This application claims priority to U.S. patent application Ser. No. 09/662,706 filed Sep. 15, 2000, which claims priority to U.S. Provisional Patent Application No. 60/154,215 filed on Sep. 16, 1999, both of which are herein incorporated by reference in their entirety.

FIELD OF THE INVENTION

This invention relates to an apparatus for the treatment of a organic fluid wherein the apparatus provides a sealed system thereby reducing the possibility of contamination.

BACKGROUND OF THE INVENTION

Various treatments have been proposed for the treatment of mammalian blood ex vivo to condition the blood in some way before injecting the blood into a patient. Some procedures take blood from a patient, condition the blood, and then return the blood to the same patient continuously. These procedures contrast with procedures which require that the blood be taken from the, patient to be treated as a batch and then returned to the patient. In batch processes there is the possibility that the blood will be given to the wrong patient as well as the dangers inherent in transferring blood from one location to another. Also, batch treatments are potentially hazardous because of the risk of blood contamination during the process of conditioning the blood, because of the risk for cross contamination between batches, and also because of the potential for infecting the operator accidentally.

A blood treatment process using batch treatment techniques involves three main steps. Firstly, the blood is sourced either from a donor or from a patient, who will also be the patient receiving the conditioned blood. The blood may be mixed with an anticoagulant and the blood charge must then be transferred to apparatus used to condition the charge. In a second step, the blood is conditioned. Finally, in a third step, the conditioned charge has to be collected and prepared for injection into the patient. These steps may involve the use of needles (sharps), tubing, valves, syringes and ancillary parts and connectors. At every stage it is important to minimize risk so that the charge is moved and treated without contamination, and so that none of the charge comes into contact with the operator running the procedure and so that none of the charge comes into contact with non-disposable parts of the apparatus.

Accordingly, it is among the objects of the present invention to provide a process and apparatus for receiving a blood charge, conditioning the charge, and preparing the conditioned charge for injecting into a patient while minimizing the risk of contamination and spillage.

It is another object of the present invention to provide a needle assembly wherein a first end of a needle may be inserted intramuscularly while a second end in fluid communication with the first end projects beyond the patient's tissue for connection to a fluid delivery or removal assembly and the second end being shielded.

It is another object of the present invention to provide a heat sealing for a thermoplastic medical tubing, thereby providing a sealed system and thus reducing the risk of contamination of the blood charge, reducing the risk of cross contamination between blood charges, and reducing the risk of the charge contacting the operator.

SUMMARY OF THE INVENTION

In accordance with one aspect of the present invention, a closed system for removing a organic fluid from a patient, conditioning the organic fluid, and returning the organic fluid to the patient is described. The system includes an apparatus for removing the organic fluid from the patient, a container for receiving the removed organic fluid, a cabinet for conditioning the organic fluid in the container, and an apparatus for delivering the conditioned organic fluid to the patient, wherein the system prevents contamination between removal of the organic fluid from the patient and delivery of the organic fluid back to the patient.

In accordance with another aspect of the present invention, an apparatus for conditioning of a organic fluid includes a cabinet for conditioning the organic fluid, an input system, and an output system. The cabinet includes a removable container for receiving the organic fluid for conditioning treatment thereof. The container includes an input port and an output port. The input system for transporting said organic fluid through an input tube from a source to said input port of said container, wherein said input tube provides sealed transportation from said fluid source to said input port of said container. The output system including a syringe for receiving said organic fluid from said output port of said container, wherein an output tube connects said output port to said syringe, the output system further including a heat sealing device disposed between said output port and said syringe for substantially severing and sealing said tubing.

In accordance with a further aspect of the present invention, a method for removing a organic fluid from a patient, conditioning the organic fluid, and returning the organic fluid to the patient without contamination includes the steps of:

removing the organic fluid from the patient;
receiving the removed organic fluid in a container;
conditioning the organic fluid in the container; and
delivering the conditioned organic fluid to the patient, wherein contamination of the organic fluid, contamination of the conditioning apparatus, and contamination of the operator are prevented between removal of the organic fluid from the patient and delivery of the organic fluid back to the patient.

In yet another embodiment there is provided a method and device for heat sealing medical tubing, thereby preventing contamination of the fluid within the tubing, potential contamination to an operator, or contamination of reusable parts of the device. In addition, there is provided a device for shielding the non-sterilized heat sealed tubing ends thereby protecting the operator from contamination from the non-sterile surfaces.

In accordance with another aspect of the present invention, a needle assembly for delivering or removing multiple fluids includes a needle device and a first fluid delivery or removal assembly. The needle device includes a first body having a needle with a first tissue penetrating end, a second fluid receiving end in fluid communication with the first tissue penetrating end, and a chamber which surrounds the second end. The first fluid delivery or removal assembly has a fluid chamber and is configured to be received in the chamber of the needle device with the second end penetrating into the fluid chamber.

BRIEF DESCRIPTION OF THE DRAWING FIGURES

There will now be described preferred embodiments of the invention, with reference to the drawings, by way of illustration, in which like numerals denote like elements and in which.

DESCRIPTION OF THE PREFERRED EMBODIMENT(S)

Figure 1:
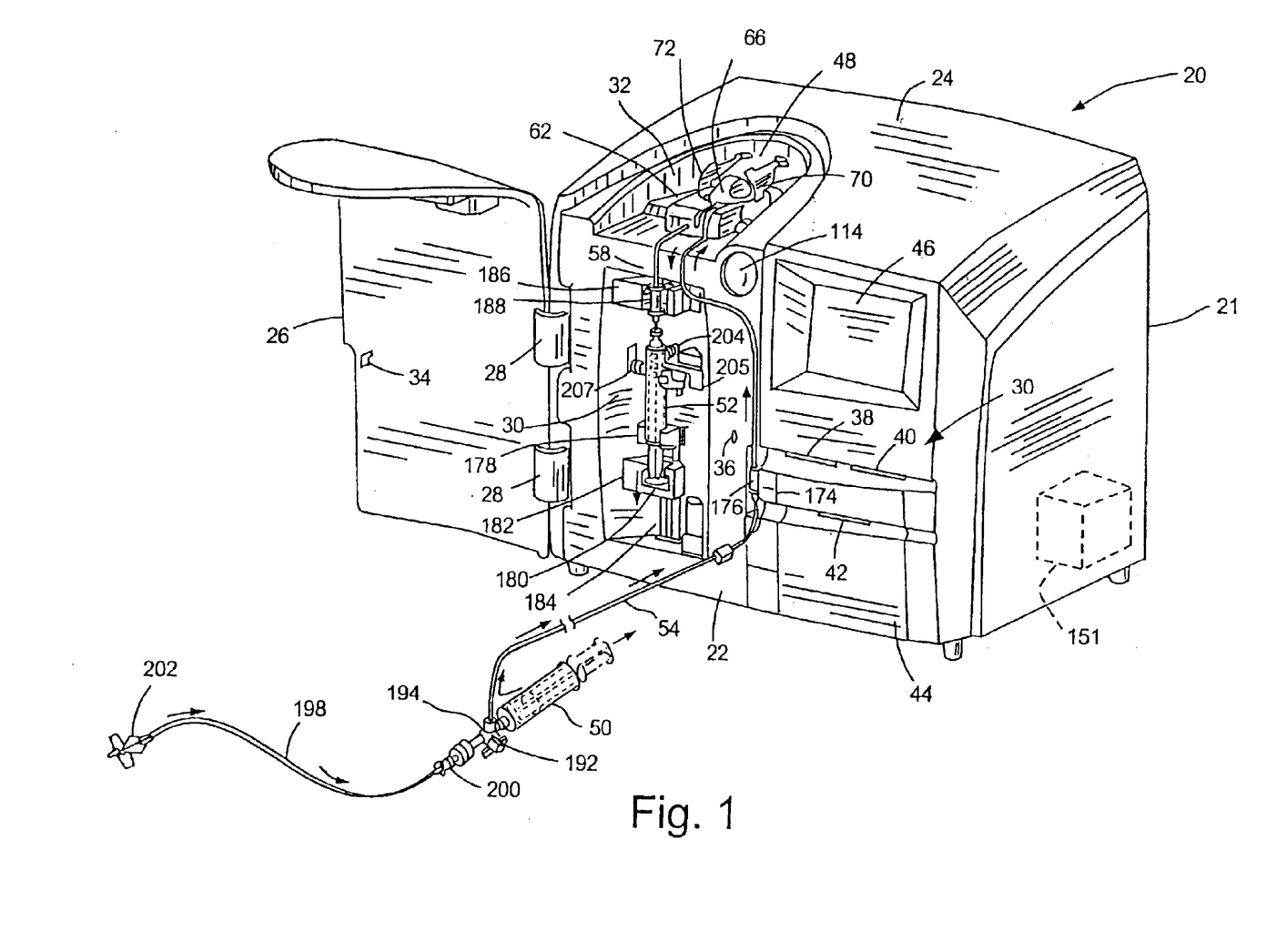
FIG. 1 is an isometric view of apparatus used in practicing a process of conditioning blood charges in accordance with a preferred embodiment of the invention and including a cabinet.

The invention will be described initially with reference to FIG. 1, which shows the apparatus generally, and then more detail will be given with reference to further drawings. As seen in FIG. 1, apparatus, designated generally by the numeral 20, includes a cabinet 21 having a front 22 and an inclined top 24. A hinged door 26 is attached to the cabinet 21 to one side of the front to move about vertical hinges 28 between an open position shown in FIG. 1, and a closed position (not shown) where it covers a front recess 30 and a top depression 32. The door is equipped with a locking bar 34 which engages in a recess 36 where it can be retained to hold the door in the closed and locked position to create a secure environment inside the cabinet 21.

As will become evident from further description, the apparatus 20 is shown after it has been prepared for use to condition a blood charge in accordance with the process of the invention. The apparatus 20 will be described in this position to provide a general understanding of the apparatus and then in more detail with reference to the process and subsequent Figures.

The cabinet 21 is designed to be secure while the charge is being conditioned. As will be explained. The apparatus 20 includes an identification system 37 so that the apparatus 20 can be used by an operator only after a patient has been designated and identified by the apparatus by way of a discrete smart card (not shown) which has to be inserted by the patient or operator in a first slot 38. A second smart card or operator's smart card is inserted by the operator in a second slot 40. The patient keeps the patient's smart card or the card is attached to the patient by a locking bracelet so that the apparatus can be used only by the operator in the presence of the patient until the apparatus is ready to treat another charge. The smart cards can be used to store data developed during operation of the apparatus and can become a permanent record of the procedure. A third slot 42 in a printer door 44 will produce a printed record of the treatment as required.

According to alternative embodiments of the invention, the smart cards may be replaced by other readable identifiers, such as tokens, keys, bar codes, or other systems. In addition, the two smart cards may both be received in a single slot in the apparatus 20 or the operator card may be omitted.

The operator controls the apparatus using a graphical display terminal (GDT) 46 having a touch screen interface pad overlaid on the GDT. The GDT serves to interrogate the operator to ensure that every required step is completed in the required sequence. Errors and instructions are also available on the GDT. Although a GDT and touch screen has been described, other operator interfaces can also be used.

As mentioned, the door 26 can be moved into a locked and closed position to cover the front recess 30 and the top depression 32. In the position shown in FIG. 1, a sterile container assembly, designated generally by the numeral 48, has been lowered into the cabinet such that part of the assembly 48 can be seen projecting upwardly into the depression 32. An input syringe 50, and an output syringe 52 have been removed from the assembly 48 ready for use. The input syringe 50 is used to source a charge and pass the charge through thermoplastic inlet tubing 54 to a container 56 which can be seen in FIG. 2. After treatment in the container 56, the conditioned charge is drawn through outlet tubing 58 from the container 56 into the syringe 52 by an actuator 182, as will be explained later.

The sterile container assembly is preferably a disposable assembly used for only a single patient to prevent charge contamination, cross-contamination between charges, or operator contamination. The term container as used herein is intended to include any container configured to receive a charge for treatment, such as a flask. The container may be rigid or flexible, such as a container in the form of a flexible bag.

The term contamination as used herein is intended to include any one or more of the following a) contamination of the charge from an exterior environment; b) contamination of the reusable parts of the treatment apparatus which may result in cross contamination between charges of different batches; c) contamination of the operator; and d) contamination of the exterior environment from a charge.

Figure 2:
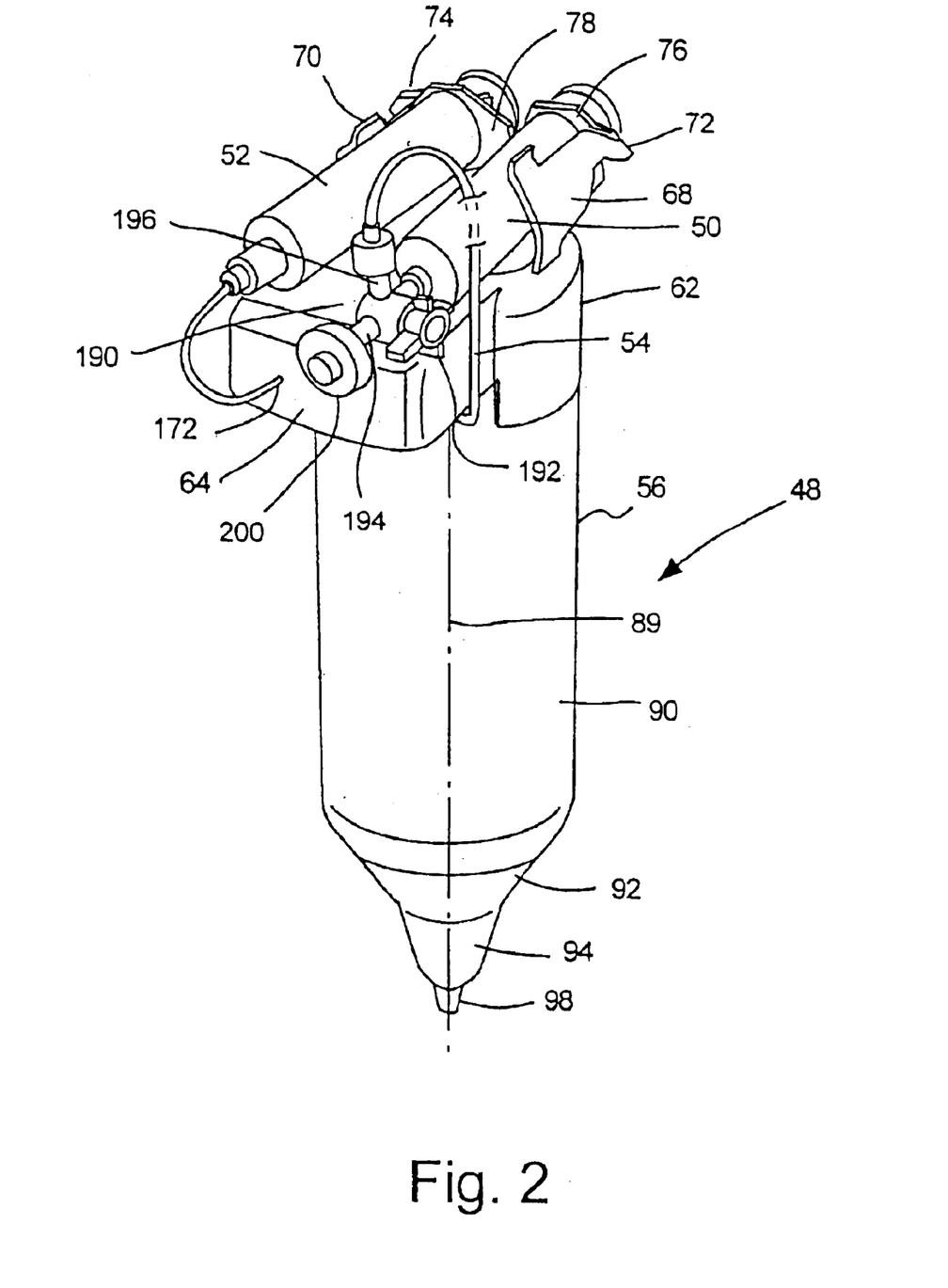
FIG. 2 is an isometric view of a disposable container assembly adapted for use with the apparatus.

For the moment it is sufficient to understand that there are three stages to the treatment. Firstly, the charge is sourced and passed by syringe 50 to the container 56 (FIG. 2). Next, treatment takes place in the container 56 and then the conditioned charge is drawn automatically from the container into the output syringe 52 ready for injection into the patient. All of these steps are controlled by the apparatus 20 in such a way that there is a limited risk of contamination. The risk of contamination is substantially eliminated by the elements of the system which will be described herein including the heat sealing of the charge carrying tubes and the needle assembly. Further the patient is identified by the identification system 37 in such a way that if the charge is sourced from the patient for subsequent return to that patient, the treated charge will be available only when the patient presents his/her smart card to thereby ensure that the right patient gets the charge.

Reference is next made to FIG. 2 to describe the main features of the container assembly 48 as it would appear in a sterile condition ready for placement in the cabinet 21 (FIG. 1). The container assembly 48 will be supplied in a sterile container which may also include most of the items needed for the procedure. These may include needles, tubing, gauze etc. as is commonly done in medical procedures requiring sterile items for the procedure.

The assembly 48 is made up of two main parts, namely the container 56 and a connector assembly 62 which serves to carry components used in the treatment procedure. The assembly 48 is shown as it would be placed in the cabinet 21 (FIG. 1), with the input syringe 50 and output syringe 52 mounted side-by-side on the connector assembly 62. It will be seen that the connector assembly includes an overhanging portion 64 which will meet parts of the apparatus contained in the cabinet 21 when the container assembly 48 is lowered downwardly into the cabinet 21. As will be described, electrical and gas connections are made automatically when the assembly 48 moves into its final position in the cabinet 21. Also, the overhanging portion 64 provides clearance under the portion 64 to allow the inlet tubing 54 to be fed from the input syringe 50 to a supply probe 65 (FIGS. 3 and 4).

The syringes 50 and 52 are conveniently stored on the connector assembly 62 between a central shaped mound 66 (FIG. 1) and respective locators 68 and 70 which are sufficiently flexible to allow the syringes to be engaged and held in place. Further location is provided by respective channel portions 72, 74 which receive respective flanges 76, 78 on the syringes 50 and 52. This interengagement locates the syringes 50, 52 longitudinally but does not interfere with vertical removal of the syringes 50, 52.

Figure 3:
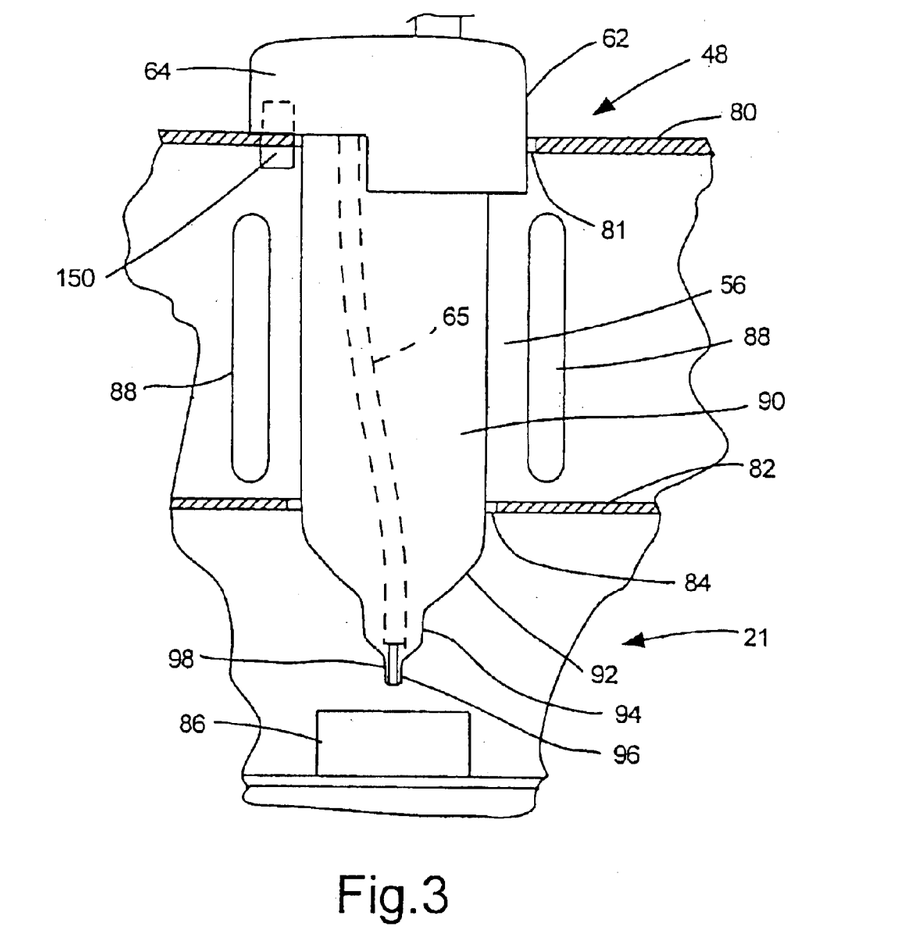
FIG. 3 is a schematic side view of the container assembly in position in the cabinet and showing structure used to condition the charge.
Figure 4:
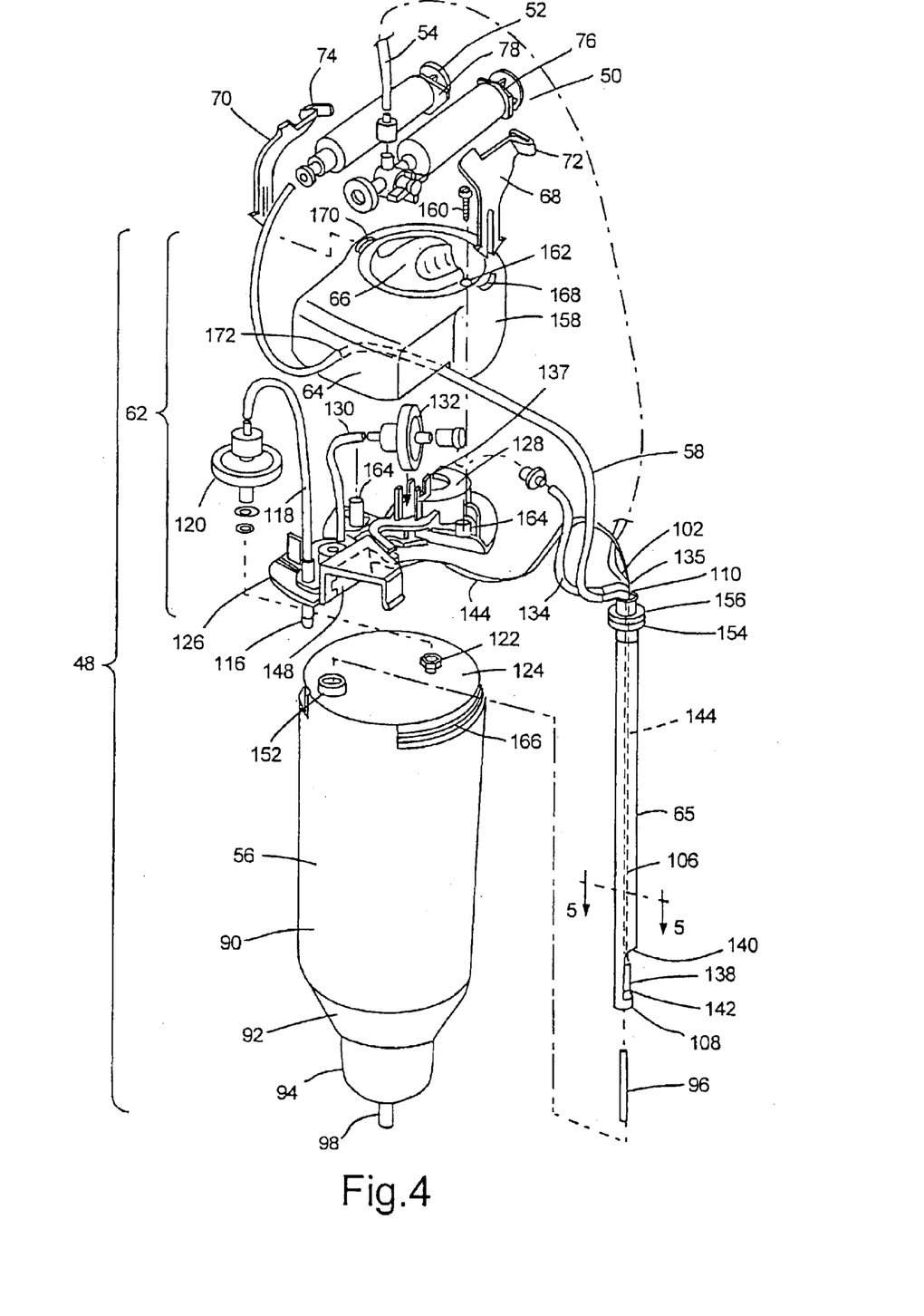
FIG. 4 is an exploded isometric view of the container assembly showing details of the construction.

As seen in FIG. 3, the container assembly 48 is located in the cabinet 21 by a shelf 80 having an opening 81 for the container 56, and below the shelf, a locator 82 having an opening 84 which is also proportioned to receive the container 56 loosely. The connector assembly 62 rests on the shelf 80 about the opening 84 to locate the container assembly 48 vertically and in proper relationship with two of the stressors to which the charge is to be subjected. One of these stressors is heat supplied by an infrared (IR) heater 86, another is ultraviolet (UV) light provided by an UV radiator 88 positioned about the container 52. Also, in the process of lowering the container assembly 48 in the cabinet 21, the overhanging portion 64 of the connector assembly 62 brings electrical connectors and gas supply connections together as will be explained after describing FIG. 4.

FIG. 3 also shows the shape of the container 56. It extends about a longitudinal axis 89 and has a generally cylindrical main portion 90. A transitional portion 92 extends from the portion 90 to a cup 94 proportioned to receive about 12 ccs of charge from the input syringe 50 (FIG. 1).

Figure 5:
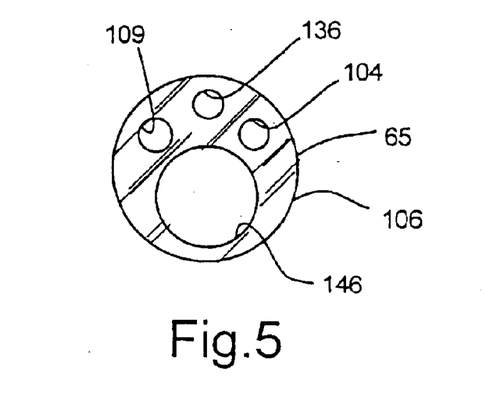
FIG. 5 (drawn adjacent FIG. 3) is a sectional view on line 5—5 of FIG. 4 and drawn to a larger scale.

The supply probe 65 will be described more fully with reference to FIG. 5. For the moment it is sufficient to understand that the function of the probe 65 is to supply charge to and remove conditioned charge from the container 56. Also, a mixture of ozone and oxygen is fed though a lumen in the probe 65 and a temperature sensor is provided in the probe 65. Heat from the IR heater 86 causes the charge to heat and that together with the gas supply, causes the charge to bubble and fill the container 56. The large surface area so formed is then subject to UV light from the radiator 88. These stressors are used to condition the charge before it is delivered by the apparatus to the output syringe 52, (FIG. 1).

The probe 65 is located centrally in the cup 94 by a solid extension 96 at the end of the probe 65. The extension fits closely inside a cylindrical socket 98 formed in the bottom of the container 58, and extending from the cup 94. The extension 96 is placed in the socket 98 during assembly and the socket is crimped from the outside to retain the extension 96 in the socket 98 and to thereby secure the supply probe 65 in the container 56.

The container 56 according to one embodiment of the invention is essentially an envelope made by blow molding a parison of low density polyethylene (LDPE) and has an internal volume that is about 70–100 times that of the charge. The walls are translucent to allow penetration of the UV and IR light stressors.

Reference is next made to FIG. 4 which is an exploded view of the container assembly 48 with the syringes 50 and 52 included. This assembly includes parts of substantially several systems. Firstly an input system made of parts associated with receiving a charge and placing it in the container 56 ready for conditioning it. Next, an output system is made up of parts related to extracting the conditioned charge from the container 56, and lastly, parts related to gas supply and recovery system.

The charge is received in the input syringe 50 which is connected by the thermoplastic tubing 54 to an elbow 102 forming part of the probe 65. This elbow leads to an intake lumen 104 formed in an extruded main body 106 which can be seen in the cross-sectional view, FIG. 5. This view is taken on line 5—5 of FIG. 4. The intake lumen 104 extends to a leading end 108 of the probe adjacent the extension 96. Consequently, the charge can be fed into the cup 94 of the container 56 by actuating the syringe 50 to move the charge through the inlet tubing 54, through the elbow 102, and then via the lumen 104 into the cup 94. Alternatively, the charge can be moved through the tubing 54 to the cup 94 by other means such as a peristaltic pump, gravity, vacuum, or other means.

The second set of parts is related to the removing the conditioned charge. The syringe 52 is the prime mover so that when it is actuated, the charge is drawn from the cup 94 into a return lumen 109 at the end 108 of the probe 65. The charge then passes through the lumen 109 leaving via an elbow 110 which in turn leads to outlet tubing 58 and to the syringe 52.

The third set of parts mentioned above relate to a gas supply and recovery system which creates ozone from oxygen and supplies and removes an ozone/oxygen mixture. Oxygen from a replaceable oxygen supply cartridge 114 passes through an ozone generator (not shown) built into the cabinet 21 (FIG. 1). Connections to the container assembly 48 are made automatically when the assembly 48 is lowered into the cabinet as described previously. To facilitate these connections, a pair of nipples 116 (one of which can be seen in FIG. 4) engage in suitable receptors (not shown) in the cabinet. The nipple that can be seen in FIG. 4 is connected to gas exhaust tubing 118 which leads to an in-line filter 120 having fittings for sealably connecting to a cup 122 formed in a top 124 of the container 56. The exhaust gas from the process is carried by these parts to an exhaust system as is conventional when using ozone.

The connector assembly 62 includes a moulded platform 126 shaped to carry the various components. As indicated in FIG. 4, the outlet filter 120 is normally mounted in a holder 128 shaped to receive the disk-shaped filter 120.

The connection to the gas supply is made using the hidden nipple 116 which supplies gas to a gas inlet tubing 130. In turn, the tubing 130 directs gas to an in-line filter 132 which is associated with standard connections to send the gas to a gas supply tubing 134. The filter 132 is arranged to engage in a support 137 formed in the platform 126, and an elbow 135 on the probe 65 is connected to the tubing 134 to lead the gas to a gas lumen 136 in the extruded probe main body 106. This lumen, like the intake lumen 104 and return lumen 109, leads to the end 108 of the main body which will be submerged in the charge when the charge is entered through the lumen 104.

The probe 65 also locates a temperature sensor 138 exposed near the end 108 through a side opening 140 cut into the side of the main body 106. A sterile sleeve 142 of very thin film plastic material encloses the sensor, but because the sleeve 142 is thin, there is a rapid temperature transfer to allow the sensor 138 to respond quickly to changes in temperature.

The sensor 138 is connected by conductive ribbon 144 which extends through a larger lumen 146 (FIG. 5) in the probe 46, and then to a connector 148 mounted on the platform 126. This connector 148 is adapted to engage a corresponding sliding connector 150 (FIG. 3) mounted in the shelf 80 of the cabinet 21. The connector 150 cooperates with the connector 148 to connect the temperature sensor 138 to a control system indicated generally at 151 in FIG. 1 and contained in the cabinet 21 (FIG. 1).

The assembled supply probe 65 is passed through a receiver 152 formed in the top 124 of the container 56, and the extension 96 at the leading end of the probe 65 is maneuvered into the socket 98 under the cup 94 of the container 56. The socket 98 is then crimped from the outside sufficiently to positively locate the extension, and hence the probe, relative to the container 56. At the same time a seal 154 under a collar 156 on the outer end of the main body 106 is brought to bear against the receiver 152 and held in compression while the socket 98 is crimped. As a result the probe is sealed in the container with a gas tight seal.

After this assembly, the platform 126 and the parts mounted on the platform are attached to a cover 158. This is done by the use of two self-tapping screws 160 (one of which is shown) which pass through openings 162 and engage in respective bosses 164 formed in the platform 126.

The sub-assembly of the platform 126 and the cover 158 is then attached to the container 56 using snap-fitting structure 166 formed on the container 56 and on the cover 158. This structure is discontinuous around the container so that there is only one way to attach the sub-assembly to the container 56 thereby ensuring that the parts line up correctly to engage the cup 122 on the container 56 and to provide the necessary clearance under the overhanging portion 64 of the connector assembly 62 for the various tubing, gas connections and electrical connections.

The container assembly 48 then receives the syringe locators 68 and 70 which snap into respective slots 168, 170 formed in the top of the cover 158. The outlet tubing 58 is then fed through an opening 172 at the back of the cover 158 and attached to the syringe 52. Similarly, the inlet tubing 54 is attached to the syringe 50 and the syringes are engaged on the cover 158 to be held in place (as previously described) by the combinations of the mound 66 with the respective locators 68 and 70.

The completed container assembly 48 is sterilized and packaged for use as mentioned earlier.

The main structural details have been described. Some details have been omitted because they are more readily described with reference to the process of conditioning the charge using the apparatus. That process will now be described and those parts of the structure that have not been mentioned will be included in this part of the description.

The process in general is designed to source suitable organic fluid either by using compatible blood or by using blood taken from a patient who is to receive the treated blood. This process will be described for the latter case but is not to be limited to that case.

The apparatus must be readied for use by placing the operator's smart card in the slot 40. A patient's smart card comes with the package containing the container assembly 48 and the operator or patient places the patient's card in the slot 38. The GDT 46 then proceeds to present instruction, error messages, and comments as the procedure progresses.

Once this is done, the door 26 is unlocked by the control circuit, and a new container assembly 46 is removed from its sterile package and lowered into a cavity in the cabinet to take up the position shown in FIG. 1 and further illustrated in FIG. 3. At this point the syringes 50, 52 are in place on the connector assembly 62, as shown in FIG. 2.

Next the input syringe 50 is lifted from its position on the connector assembly 62 and placed conveniently with the inlet tubing 54 passing through a heat sealing device 174 which is attached to the cabinet 21 for use to seal and substantially sever the inlet tubing 54 as will be explained. The inlet tubing 54 has a locator 176 mounted on the tubing to position the inlet tubing 54 in the device 174.

The output syringe 52 is then removed in similar fashion and placed vertically as shown in FIG. 1. The syringe 52 is located in a fixed mount 178 using the flange 78 and a syringe operator 180 extends downwardly and is engaged in an actuator 182 which can be driven along a slide 184 by a motor and drive (not shown) in the cabinet. This operation will be described with reference to removing a conditioned charge.

The outlet tubing 58 associated with the syringe 52 is led through a second heat sealing device 186. The heat sealing device 186 includes a locating body 705 positioned on the tubing 58 which positions the outlet tubing between jaws of the heat sealing device 186. This device 186 will be used after the conditioned charge is drawn into the syringe 52, as will be explained.

A message on the GDT 46 (FIG. 1) reminds the operator to close the door 26 and the door lock bar 34 is engaged. The control system 151 (FIG. 1) activates the door so that the cabinet can be opened only by using the two smart cards. Consequently the smart card carried by the patient is necessary so that no one other than the patient can cooperate with the operator to get into the cabinet 21. The patient's smart card is preferably attached to the patient's wrist in a semi-permanent fashion using a suitable band of the type commonly used in hospitals.

The input syringe 50 is still in the condition shown in FIG. 2. A T-connector 190 includes a valve controlled by a selector 192 which connects the body of the syringe to either an in-line port 194, or a side port 196 at right angles to the axis of the body. The inlet tubing 54 is attached to the port 196 and the port 194 is available. The input syringe 50 and the associated parts are then moved to the position shown in FIG. 1.

A needle (not shown) is attached to port 194 and about 2 ccs of an anti coagulant (preferably sodium citrate) is drawn into the syringe. The needle is discarded into a sharps container and then a tubing assembly 198 (FIG. 1) is attached to the in-line port 194. This assembly 198 includes a one-way valve 200, to avoid back flow, and at its leading end an angel wing collector set 202 is ready for engagement into the patient to collect blood. The collector set is used to draw 10 ccs of blood into the syringe 50 where it is mixed with the sodium citrate by rocking the syringe gently to create a blood charge for treatment in the process according to the invention.

Next, the selector 192 on the T-connector 190 is operated to connect the body of the syringe 50 with the side port 196 leaving the tubing assembly attached but inoperable. The syringe 50 is then inverted (i.e. placed with the T-connector uppermost) and about 3 to 4 ccs of sterile air are drawn from the container 56 into the syringe. The syringe 50 is then again inverted so that the air is above the charge and the syringe is then operated to drive the charge through the inlet tubing 54 and into the container 56 driven by the air in the syringe. As a result the inlet tubing is cleaned out as the air follows the charge.

It is now time to discard the input syringe 50 and associated parts. Before this can be done, the syringe 50 has to be separated from the cabinet 21 to which it is connected by the inlet tubing 54. This is achieved by operating the heat sealing device 174 which seals and substantially severs the tubing under the influence of heat. The structure and operation of heat sealing devices will be described in further detail below with reference to FIGS. 9–17.

Once this step is completed the input syringe 50 and attached parts are discarded.

It should be noted that the door 26 (FIG. 1) has not been opened during this procedure and that the charge of blood and sodium citrate has been received in the cup 94 of the container 56 (FIG. 3). It should be noted that although the process is to condition blood, to be accurate the process treats blood as the prime part of a charge which also contains an anticoagulant, (or any other additive). Consequently the term "charge" is used to describe a batch made up of blood and at least one additive. However if circumstances arise in which blood can be treated alone, such use is within the scope of the term because organic fluid continues to be the subject of the treatment and it is not intended to exclude such an interpretation. Although the term fluid has been used herein, it is expected that primarily liquids will be treated with the apparatus of the present invention.

The next stage of the process can now begin. The control system 151 in the cabinet 21 takes over and starts the IR heater 86 (FIG. 3) to elevate the temperature of the charge. This is one example of a process known generally as "stressing" the charge and the IR radiator is known as a "stressor". The temperature is elevated to about 42.5 C and is controlled from a reading originating with the temperature sensor 138. Once the selected temperature has been reached, the control system activates a second stressor. An ozone generator sends an oxygen/ozone mixture into the container 56 through the probe 65 as described earlier. Also, the UV light source 88 (third stressor) is activated so that the heated charge is simultaneously stressed by the ozone/oxygen mixture and by the UV light simultaneously for about 3 minutes. The bubbled charge fills the container and is then allowed to settle and cool for a period of time. In one example, the charge settles and cools for about 7 minutes so that bubbles in the charge will tend to settle.

At this point the charge has been conditioned and the GDT 46 (FIG. 1) will respond to the control system to give the operator a message that the smart cards will be needed to withdraw the conditioned charge. However the door 26 (FIG. 1) will not open until the charge is available in the output syringe 52 even if the cards are inserted at this stage. On the other hand, if the charge is in the syringe (as will be explained) and ready for removal, the door 26 will remain closed unless the cards are inserted.

Next the apparatus will commence the step of moving the charge from the container 56 (FIG. 3) to the output syringe 52 (FIG. 1). This is done automatically by the actuator 182 seen in FIG. 1, which draws the operator 180 downwardly. When all the fluid has been withdrawn from the container 56 into the syringe 52, considerable amounts of gas are aspirated therein. In the case of foaming liquids, such as blood, the air is contained in persistent bubbles which do not settle rapidly and must be removed. To this end, a knocker 204 is disposed adjacent to the syringe 58 whose purpose is to apply sudden accelerations to the syringe. For best effect, the syringe 58 is constrained radially only very loosely through the use of soft elastomeric supports, such as a coil spring 207. According to one example, the syringe can translate 8 mm with less than 1 N force applied by an impact tool 205. The effect of the sharp shocks delivered by the knocker 204, is to rapidly accelerate the syringe barrel radially. The inertia of the fluid film in the bubbles causes their structure to be disturbed by the rapidly moving walls and one observes a general collapse of the bubbles after a number of shocks have been delivered.

Although any impulse delivering electromechanical system will perform the function of the knocker 204, one preferred embodiment includes a rotary impact tool 205 positioned on a rotating arm. An elbow, of the rotating arm is provided with a torsion spring and the hand of the arm is provided with a roller. The device rotates in a volute or spiral cavity so that as the arm rotates, energy is stored in the torsion spring until a release point is reached and the arm rapidly deploys its energy in impacting the syringe 58. The frequency of the knocker 204 can be varied and will to some extent depend on the geometry and mass of the parts. However, it has been found that a frequency of 1 Hertz provides good results. A sensor for determining when the bubbles have been eliminated from the charge is described in U.S. patent application Ser. No. 09/811,260, filed on Mar. 16, 2001, which is incorporated herein by reference in its entirety.

Next the actuator 182 is operated to express some of the contents of the syringe 52 back into the outlet tubing 58 until there remains a volume of 9 to 10 ccs of conditioned charge. A sensor (not shown) in the heat sealing device 186 tells the control system in the cabinet 21 that the system is ready to seal the outlet tubing 58 in similar fashion to the seal made on the inlet tubing 54 as previously described.

Although a preferred embodiment of the present invention includes one or more heat sealing devices, it should be understood that the syringe 52 is separated from the container 48 by severing the tubing 58 for purposes of convenience and that the heat sealing step is not necessary if a longer piece of tubing 58 is used.

Referring now to FIGS. 9–12 there is shown one embodiment of the heat sealing device 186. The heat sealing device 186 includes a locating body 705 positioned on a tubing 58 and first and second heat sealing jaws 710. The locating body 705 is comprised of a first body 720 and a second body 730 wherein the inner bore 732 of the second body 730 is adapted to receive the first body 720. The first and second bodies 720, 730 each include two apertures 707 adapted to receive the sealing ends 712 of the first and second heat sealing jaws 710. The first and second bodies 720,730 respectively, further include apertures 721,731 respectively for receiving the medical tubing 58. The locating body 705 is preferably a disposable element connected to the medical tubing.

The heat sealing jaws 710 may be formed of steel, stainless steel, titanium, copper, brass, Nitinol, ceramic or similar materials which have good heat conductive properties. In one embodiment, the jaws 710 are formed of copper having resistive heating wire, such as Nichrome wire, wrapped thereabout. Thus in use, a current is applied to the Nichrome wire, thereby generating heat which is conductively transferred to the copper jaws 710. Alternatively, the jaws 710 may include a firerod (not shown) disposed within a bore, wherein a current is passed through the firerod thereby generating heat which is conductively transferred to the jaws 710. In another embodiment, a transistor may be used to heat each of the jaws 710. If a transistor is used for heating, the transistor may also be used to measure the temperature of the jaws. The heat sealing jaws 710 are attached to appropriate supporting, guiding, and advancing means (not shown).

Figure 10:
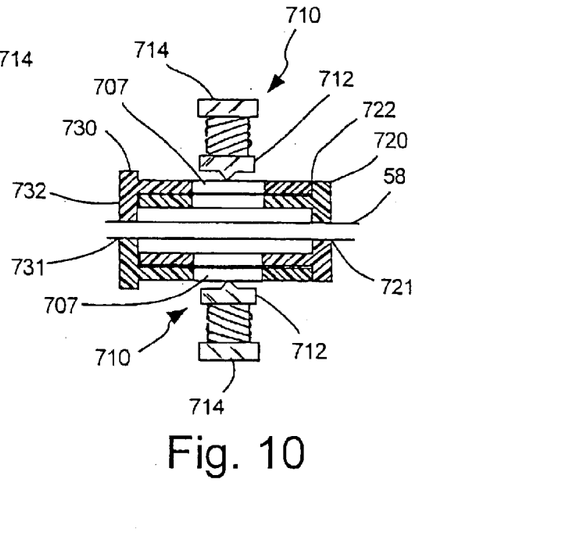
FIG. 10 is a cross-sectional top view of the heat sealing device of FIG. 9.
Figure 11:
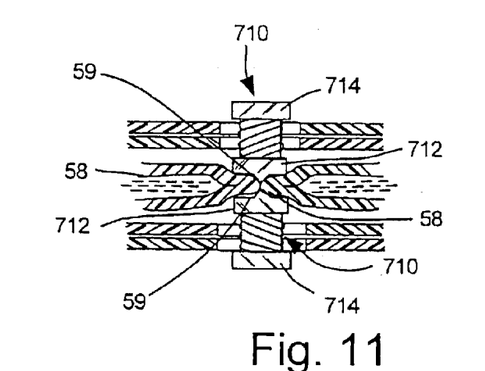
FIG. 11 is an enlarged cross-sectional top view of the heat sealing device of FIG. 9 having the heat sealing jaws in an advanced position.

Referring now to FIG. 10 there is shown a cross-sectional view of the heat sealing device 186 wherein the first body 720 is disposed within the bore of the second body 730 and the tubing 58 passes through the apertures 721 and 731. The proximal ends 712 of the heat sealing jaws 710 are advanced as shown in FIG. 11 until they contact the tubing 58. After contacting the tubing 58 the jaws 710 are advanced until the proximal ends 712 touch or nearly touch. Prior to or during the process of advancing the jaws, the jaws 710 are heated. A protruding rib 716 on each of the jaws 710 substantially severs the tubing 58. Thus, the tubing 58 is pinched, sealed, and substantially severed by the hot jaws 710. The jaws 710 are then cooled and retracted from the apertures 707. The jaws 710 should preferably be held in contact with the tubing 58 until the tubing has cooled from a molten to a solid state to form a seal on the two substantially severed ends of the tubing.

Figure 12:
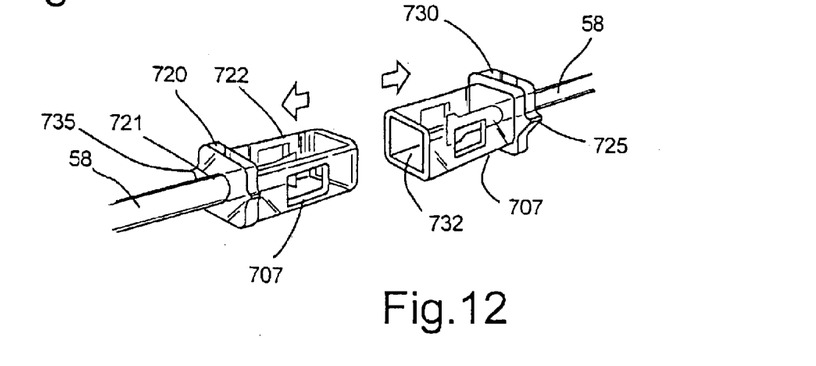
FIG. 12 is an exploded view showing the separation of the tubing and locator device after heat sealing with the heat sealing device of FIG. 9.

Referring now to FIG. 12 there is shown the first body 720 and the second body 730 as disassembled after sealing. As illustrated, the tubing 52 is fixedly attached at the apertures 721, 731 to the first body 720 or second body 730 respectively. Therefore, when the tubing 52 is removed from the apparatus 20, the substantially severed, heat sealed ends are protected by the first body 720 or second body 730, respectively. Because the ends are covered and protected from handling there is a lesser likelihood of contaminating the operator or contaminating the apparatus 20.

Figure 9:
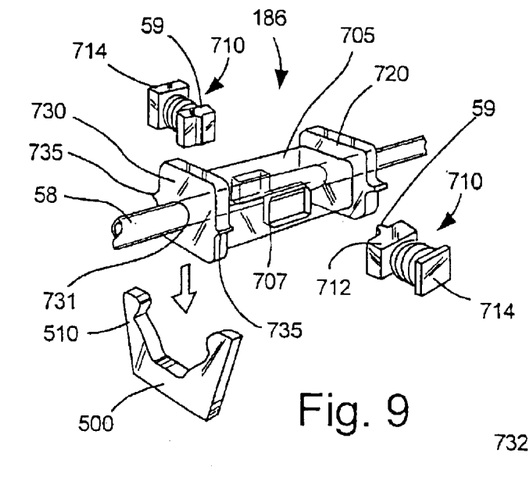
FIG. 9 is a perspective view of one embodiment of the heat sealing device of the present invention.

As shown in FIG. 9, the heat sealing device 186, may further include a location means 500. The location means 500 includes a recessed region 510 adapted to receive the projection 735 or 725 disposed on the first body 720 or the second body 730. The location means 500 provides a simple and effective method of holding and aligning the locating body 705 within the device 20. Additionally, the heat sealing process described above requires that the jaws 710 be in contact with the tubing 58 for a period of time, thus, the location means 500 provides support and alignment of the locating body 705 thereby allowing heat sealing of the tubing 58. The location means 500 may be formed of a plastic, metal or other material. The location means 500 is preferably integrally formed with the device 20. Preferably, the jaws 710 are sterilized between uses. One example of sterilization would be heating the jaws 710 in place in the apparatus 20 to about 140 degrees Celsius for about 4 minutes.

Figure 13:
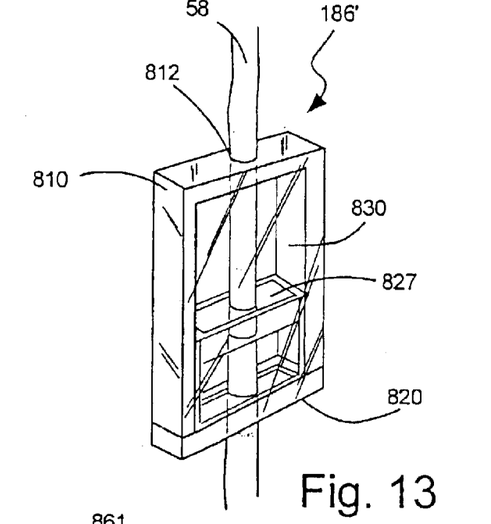
FIG. 13 is a perspective view of another embodiment of the heat sealing device.
Figure 14:
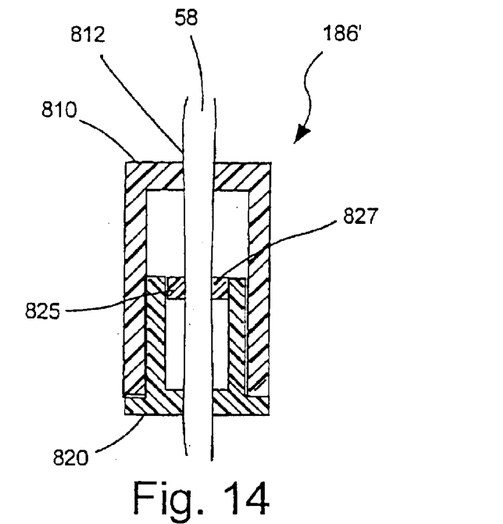
FIG. 14 is a cross-sectional view of the embodiment of the heat sealing device of FIG. 13.

Referring now to FIGS. 13–17 there is shown a second embodiment of a heat sealing device 186'. The heat sealing device 186' includes a locating device affixed to a tubing 58, shown in FIGS. 13 and 14, and heat sealing jaws 860 for sealing the tubing as shown in FIGS. 15A and 15B. The locating device shown in FIG. 13 includes a first body 810 having an aperture 812 disposed through a proximal end and a second body 820 having an aperture 822 disposed through a proximal end. The second body 820 is adapted to be received by an inner bore of the first body 810. The second body 820 includes a flange 825, which abuts the distal end of the first body 810 when the first and second bodies are assembled together as shown in FIGS. 13 and 14.

As shown in FIGS. 13 and 14 the first body 810 may be formed having a "U" shape with a foil covering 830 disposed on either side thereof. The foil 830 may be any ductile foil suitable for heating and able to act as a sterile barrier. One example of a suitable foil is a ductile aluminum foil laminate. Other barrier materials may also be used and may be secure to the first body 810 in any known manner. The second body 820 may be formed having a rectangular shape including the flange 825 disposed at the proximal end and a tubing guide 827 disposed at the distal end. As shown, the tubing 58 passes through the aperture 812 where the tubing is fixedly attached to the first body 810 with a compatible adhesive, and similarly attached to tubing guide 827 on the distal end of the second body 820. The tubing 58 and guide 827 are able to slide through the aperture 821 of the second body 820.

Figures 15A, 15B, 16, 17:
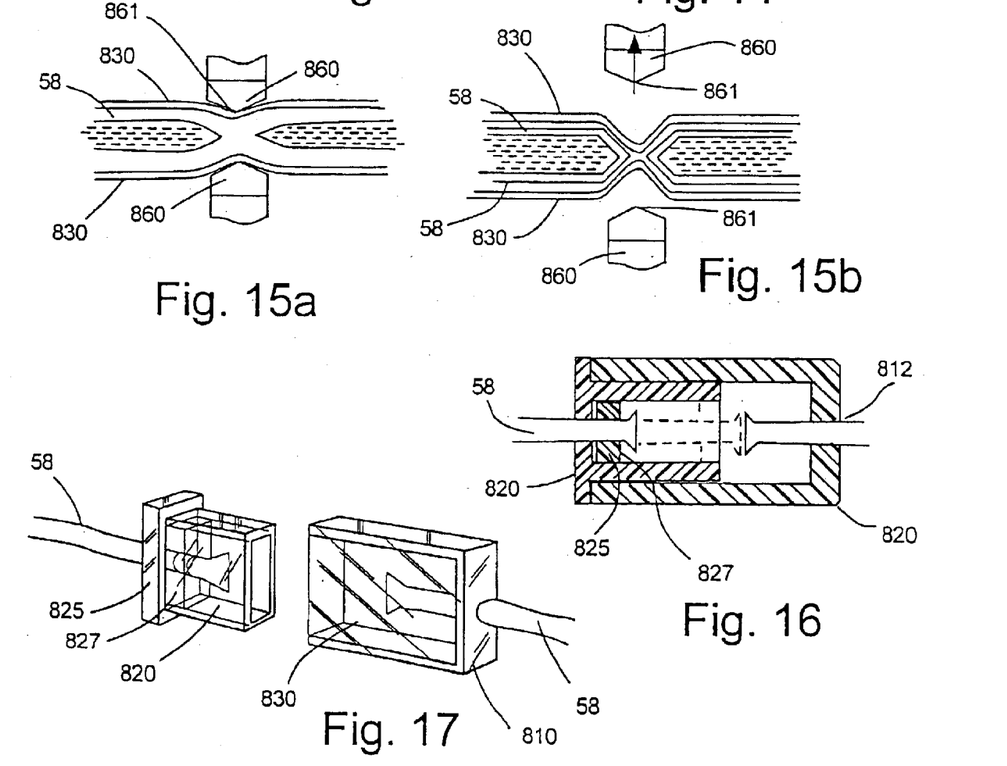
FIG. 15A is a cross-sectional view illustrating the heat sealing jaws of FIG. 13 advanced into a sealing position.
FIG. 15B is a cross-sectional view illustrating the heat sealing jaws of FIG. 13 retracted from the sealing position after sealing the tubing.
FIG. 16 is a cross-sectional view illustrating the separation of the tubing after heat sealing with the heat sealing device of FIG. 13.
FIG. 17 is a perspective view illustrating the separation of the locator device after the tubing has been heat sealed with the heat sealing device of FIG. 13.

Referring now to FIGS. 15A and 15B there is shown the heat sealing device 186' in use. A pair of pre-heated jaws 860 are advanced as shown in FIG. 15A, the distal tips 861 of the jaws 860 are designed to converge along a line. The tubing 58 is compressed between the jaws and heat is conducted from the jaws to the tubing through the foil 830. As shown in FIG. 15B, the tubing 58 is pinched, sealed, and substantially severed by the hot jaws 860. The foils 830 serve as a barrier between the contaminated tube ends and the heat seal jaws. An advantage of the present embodiment of the heat sealer is that the jaws 860 do not contact the tubing 58 and the foil 830 provides a sterile barrier. This prevents contamination of the jaws.

In addition, the ductile foil deforms to support the molten seal zone of the tube so that the hot jaws can be withdrawn and the tube ends allowed to cool rapidly without changing shape. The use of aluminum foil allows for good cooling but other methods of cooling may also be used. Alternatively, the foils 830 may be replaced by other barriers, such as formed plastic shields which snap into stops as the tube is compressed between the jaws.

As shown in FIG. 16, after the tubing 58 has been pinched, sealed and substantially severed, the section of tubing 58 disposed through the tubing guide 827 is retracted. The tubing 58 is retracted until the tubing guide 827 rests against the proximal end of the bore 823 adjacent to the flange 825. The heat sealed end of the tubing 58 is held in this retracted position by friction or other appropriate means.

After the tubing guide 827 contacts the flange 825, further force applied to the tubing 58 will cause the second body 820 to slide out of the bore 811 as illustrated in FIG. 17. The walls 828 of the second body 820 protect the heat sealed end 57 of the tubing 58, thereby preventing an operator from touching the non-sterilized tubing.

Although the geometry of the first body 810 and the second body 820 have been shown and described in relation to the specific geometries illustrated this should not be considered limiting in any manner. The bodies defining the overall geometric shape may be formed in any manner. In addition, although two heat sealing jaws have been shown, it is also possible to use a single heat sealing jaw and an anvil to perform severing and sealing.

After the heat sealing device has sealed the outlet tubing 58 the process has now reached a critical point. If the patient or operator has not inserted the patient's smart card by now, the apparatus will wait only for a predetermined time (usually about 20 minutes) before aborting the process. If the process is to be aborted, a message will appear on the GDT 46 (FIG. 1) and the control system will cause the actuator 182 to drive the syringe operator 180 so that the conditioned charge is returned to the container 56 before shutting down the process. The heat sealer then seals the tube 58 to prevent accidental use. Once this is done the operator can open the door 26 using only the operator's card so that the container 56 and its contents can be discarded to ready the apparatus 20 for a new process.

If the patient presents the patient's card in time, the respective smart cards are inserted into the slots 38, 40 and the heat sealer 186 will seal and substantially sever the tubing 58, the door 26 will open, and the output syringe 52 is then available for removal from the cabinet 21. However, before this is done, the patient must be prepared for the injection of about 8 to 9 ccs of conditioned charge. Firstly, the patient is anaesthetized in the gluteus maximus muscle using a suitable needle and performing the standard procedure for ensuring that the needle has not been inserted into a vein. Next, the anesthetic syringe is removed and the needle is left in the patient. The output syringe 52 is fitted with the same type of hub fitting as the anesthetic syringe. The output syringe 52 is then taken to the anesthetic needle and after discarding the remaining tubing 58 from the heat sealing operation, the output syringe 52 is attached to the anesthetic needle and the conditioned charge is fed into the patient slowly. After this procedure, the output syringe and attached needle are discarded.

The apparatus can then be prepared for the next procedure by removing the remains of the container assembly 48.

It will now be evident that the process can be used to treat mammalian blood in a blood charge to provide a conditioned charge for giving to a patient in a medical procedure. In general the process includes the steps of providing an automatic apparatus for treating the blood charge to create the conditioned charge, and for presenting the conditioned charge ready for use. The apparatus has a secure environment, a door controlling access to the environment, a container, and stressors arranged to operate on a charge in the container in the controlled environment. The blood charge is transported into the secure environment through thermoplastic inlet tubing for deposit in the container, and the tubing is then sealed and substantially severed. Next the part of the inlet tubing outside the secure environment is removed and the operation of the automatic apparatus is initiated so that the stressors will operate on the charge for a predetermined period, thereby stressing the charge in the container while maintaining the secure environment. The apparatus is then given time to transport the conditioned charge from the container to a receiver, and the door is opened to provide access to the receiver for use to give the conditioned charge to the patient.

Improved control can be provided by the preferred use of smart cards, as explained, and by the use of thermoplastic tubing and heat sealers to ensure that the secure environment is maintained. Also, the process can be enhanced by use of the knocker to reduce the time needed to dissipate the bubbles in the conditioned charge.

Figure 6:
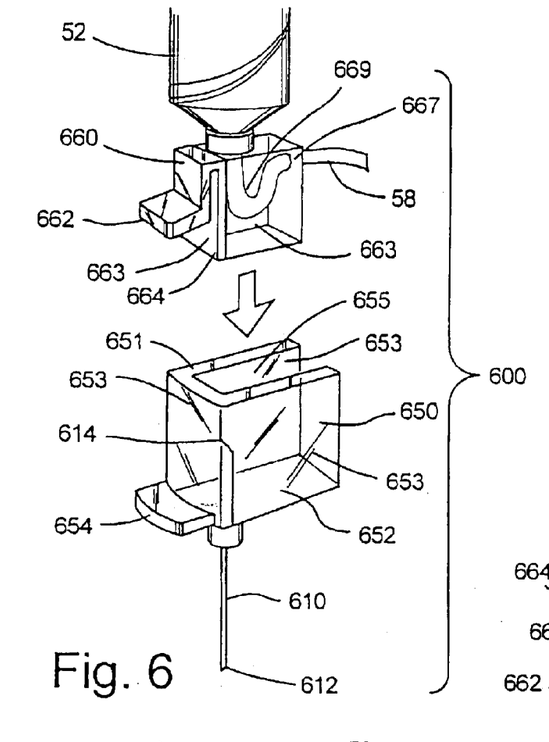
FIG. 6 is an exploded view of the needle assembly of the present invention.
Figure 7:
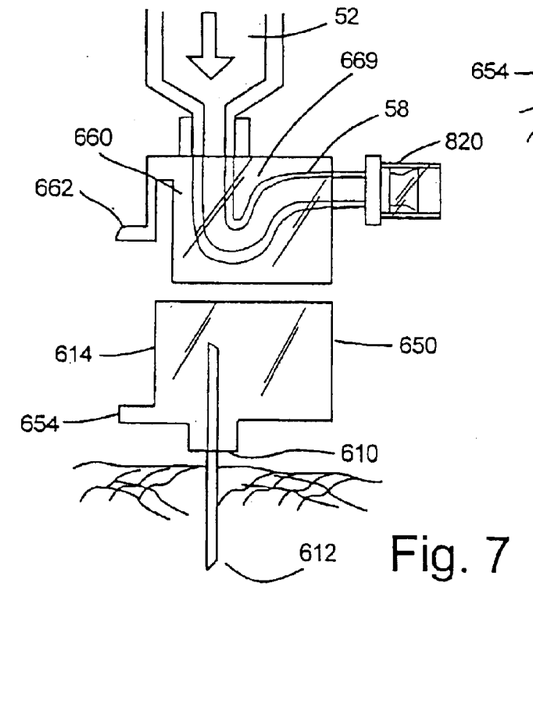
FIG. 7 is a cross-sectional view illustrating the needle assembly prior to assembly for use.
Figure 8:
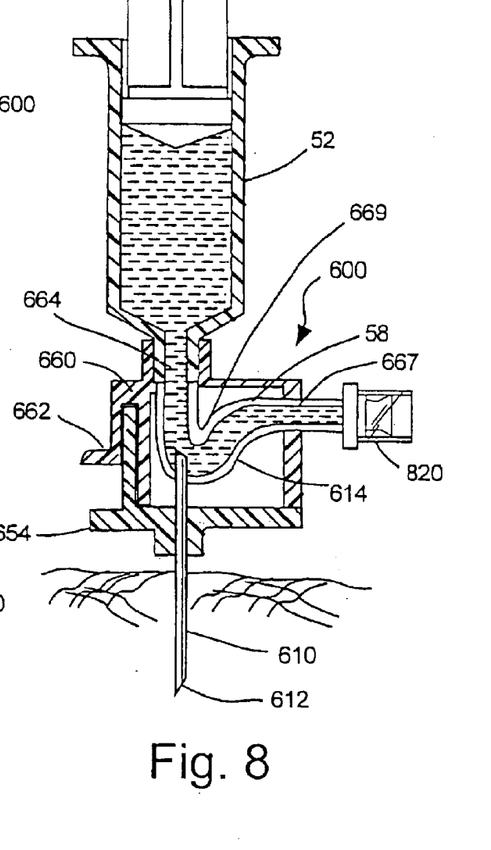
FIG. 8 is a cross-sectional view illustrating the needle assembly as assembled for use.

Referring now to FIGS. 6–8 there is shown a needle assembly 600 for use with the apparatus and methods of the present invention. After a charge has been prepared according to the process described above, the charge is injected intramuscularly back into the patient's body. Typically, this process is carried out by first injecting the patient with a local anesthetic intramuscularly, such as in the gluteus maximus. After inserting the needle, it is common practice to pull back on the syringe plunger to ensure that the needle is not placed in a vein or artery. Once the anesthetic is injected, the syringe is removed from the needle, thereby leaving the needle in place, the charge prepared above is then attached by a luer fitting (luer slip or luer lock) on the needle and injected. The disadvantage of this method is the potential of contamination to the operator and contamination of the charge when connecting the syringe containing the charge to the needle. In addition, air bubbles may become trapped between the needle and the syringe carrying the charge during connection.

Referring now to FIG. 6 there is shown the needle assembly 600 of the present invention. The needle assembly 600 includes a needle connector 650, a syringe connector 660, and a needle 610. The needle connector 650 includes a proximal end 651, distal end 652, and a handle 654 disposed adjacent the distal end 652. A plurality of walls 653 define a chamber 655. The needle connector 650 and the syringe connector 660 are configured to be connected by a press fit, however, other connections may also be used, such as a snap fit, screw connection or use of other mechanical advantage elements. The needle 610 has a first end 612 adapted to be inserted into tissue and a second end 614 within the chamber 655 adapted to receive the tubing 58.

A plurality of walls 663 define the syringe connector 660. The syringe connector 660 further includes a handle 662, a luer fitting 664, and an aperture 667 disposed through one of the walls 663 wherein the aperture is adapted to receive the tubing 58, which forms in effect a puncturable or penetratable fluid chamber of small dead volume. Other fluid chambers may also be used. As shown in FIG. 6, the distal end of a syringe 52 is connected to the luer fitting 664 of the syringe connector 660. The tubing 58 extending from the syringe is threaded through the interior of the syringe connector 660. The tubing 58 is extended out through an aperture 667. As shown in FIGS. 6–8, the tubing 58 is disposed within the syringe connector 660 forming a curve 669. Alternatively, the syringe connector 660 may be formed of multiple pieces (not shown) wherein each piece contains a pre-formed area adapted to receive the tubing 58 and retain the curve 669. As shown in FIG. 6, the end of the tubing 58 can be heat sealed according to the procedure described above. In one embodiment, the syringe connector 660 can be integrally formed with the heat seal locating body 705.

Referring now to FIGS. 7 and 8, there is shown the needle 610 of the first body having been inserted into a patient's tissue. A first needle assembly may be disposed within the patient's tissue by first connecting the needle connector 650 to a syringe fitted with a connector for connecting to the needle connector. The syringe connected to the needle connector 650 may be filled with an anesthetic, a beneficial agent, or saline. The needle assembly is then inserted into the patient's tissue, for intramuscular injections, the operator would then pull back on the syringe plunger to ensure that the distal end 612 of the needle 610 did not pierce a vein or artery. In instances where the beneficial agent to be injected is an opaque red fluid, a syringe filled with a clear fluid may be utilized for the initial insertion of the needle so that a "pull-back" test may be performed. After confirming that the needle did not pierce a vein or artery and/or after injection of the anesthetic, the first syringe and associated connector may be removed from the needle connector 650 and a second syringe 52 with the syringe connector 660 may be attached to the needle connector 650.

The walls 653 of the needle connector 650 ensure that the proximal end 614 of the needle 610 is protected thereby preventing finger sticks and contamination during exchange of syringes. As shown in FIG. 7, the wall 663 of the syringe connector 660 is received by the chamber 653 of the needle connector 650 so that the distal end 664 of the syringe connector contacts the bottom 652 of the chamber 653 thereby ensuring that the needle will pierce the tubing 58. The piercing of the tubing with the second end 614 of the needle creates a liquid/liquid interface which prevents possible contamination. Additionally, because the syringe 52 and the tubing 58 contain no air bubbles, the chance of injecting an air bubble during the exchange of syringes is greatly reduced. Also because the syringe assemblies are provided in a sealed condition, the risk of spillage of the contents of the syringes is greatly reduced, therefore reducing the risk of contamination of the contents of the syringe and the risk of contamination to the operator.

The needle connector 650 and the syringe connector 660 may be formed of a bio-compatible material such as urethane, polyvinylchloride, or similar plastics. Additionally the needle assembly 600 may be formed of a clear or opaque material thereby allowing a operator to visually confirm placement of the needle and injection of the beneficial agent. The tubing 58 may be formed of a bio-compatible material such as urethane, silicon, polyvinylchloride (PVC) or preferably polyurethane.

The combination of the needle assembly 600 and the heat sealing device allow the charge to be delivered to the patient without risk of contamination. The irreversible steps of the process including heat sealing, puncture of the tubing with the double ended needle for injection, and removal of the smart card from the patient by cutting a locking bracelet may it impossible to incorrectly or inadvertently reuse the disposable elements of the system.

Although the needle assembly has been described as employing a double ended needle, the second end 614 of the needle may be replaced with an non-piercing member, such as a cannula. In this alternative embodiment, an elastomeric port or valve would be provided on the fluid reservoir within the syringe connector 660 and the elastomeric port or valve would be penetrated by the cannula.

Although the present invention has been described with respect to the treatment of blood, it should be understood that the treatment device may be used for treatment of any organic fluid. A organic fluid includes but is not limited to the blood, oils, and fractions of blood such as, plasma, red blood cells, white blood cells, immune system cells, antibodies, macrophage, T cells, and B cells.

It will be appreciated that the described embodiments of the apparatus, and of the process associated with the apparatus, can be varied within the scope of the claims and that such variations are within the scope of the invention.

What is claimed is:

1. A closed system for removing an organic fluid from a patient, conditioning the organic fluid, and returning the organic fluid to the patient, the system comprising:

an apparatus for removing the organic fluid from the patient;

a container for receiving the removed organic fluid;

a cabinet for conditioning the organic fluid in the container; and an apparatus for delivering the conditioned organic fluid to the patient, wherein the apparatus for delivering the conditioned organic fluid to the patient includes a syringe connected to the container by tubing and a heat sealing device arranged to substantially sever and seal the tubing after delivery of the conditioned organic fluid from the container to the syringe, the syringe comprising a plunger slidable within a tube;

wherein the system prevents contamination between removal of the organic fluid from the patient and delivery of the organic fluid back to the patient.

2. The system of claim 1, wherein the apparatus for delivering the conditioned organic fluid to the patient includes a double ended needle device.

3. The system of claim 2, wherein the apparatus for delivering the conditioned organic fluid to the patient includes a syringe connected to sealed tubing, wherein the sealed tubing is configured to be penetrated by the double ended needle.

4. The system of claim 1, wherein the cabinet includes means for treating the organic fluid with at least one stressor including ultraviolet light, heat, infrared energy, ozone, and oxygen.

5. The system of claim 1, wherein the heat sealing device comprises:

a first body having a first end, a second end, and a bore extending therethrough for receiving the tube containing fluid;

a second body including a first end, a second end and a bore extending therethrough for receiving the tube containing fluid, wherein the second end of the first body and the second end of the second body are configured to engage one another; and at least one heat sealing jaw arranged to substantially sever and seal the tube between the first end of the first body and the first end of the second body, wherein the first and second bodies are arranged to separate and protect first and second substantially severed ends of the tube after the heat sealing jaw has substantially severed and sealed the tube.

6. The heat sealing device of claim 5, further comprising a flexible foil positioned on the first or second body between the tube and the heat sealing jaw.

7. The heat sealing device of claim 6, wherein the flexible foil isolates the tube from the two heat sealing jaws before, during and after a heat sealing process.

8. The heat sealing device of claim 5, wherein the first and second bodies are cup shaped members arranged to respectively contain the first and second substantially severed ends of the tube.

9. The heat sealing device of claim 5, further comprising means for sterilizing the two heat sealing jaws by heating.

10. The heat sealing device of claim 1, wherein the cabinet has a front recess providing access to the cabinet interior and a door closable to close the recess and form a closed environment of the cabinet interior, the heat sealing device being attached to the cabinet and being disposed within the closed environment when the door of the cabinet is closed.

11. An apparatus for conditioning of a organic fluid, the apparatus including:
   a cabinet for conditioning the organic fluid, the cabinet including a container for receiving said organic fluid for conditioning treatment thereof, said container including an input port and an output port;
   an input system for transporting said organic fluid through an input tube from a source to said input port of said container, wherein said input tube provides sealed transportation from said fluid source to said input port of said container; and
   an output system including a syringe for receiving said organic fluid from said output port of said container, the syringe comprising a plunger slidable within a tube, wherein an output tube connects said output port to said syringe, the output system further including a heat sealing device disposed between said output port and said syringe for substantially severing and sealing said tubing.

12. The apparatus according to claim 11, wherein the output system further includes a double ended needle device for delivery of the organic fluid from the syringe to a patient.

13. The apparatus according to claim 12, wherein the double ended needle device includes, a needle connector, a needle having first and second ends, and a syringe connector, wherein the needle connector further includes a chamber adapted to receive the syringe connector and wherein the first end of said needle projects into said chamber and said second end of said needle projects beyond a distal surface of said needle connector.

14. The apparatus according to claim 13, wherein said syringe connector further includes a means for receiving a syringe and said output tubing.

15. The apparatus according to claim 14, wherein said syringe connector comprises at least two pieces wherein each piece respectively contains a recessed area for receiving said output tubing disposed on the end of a syringe.

16. The apparatus according to claim 13, wherein said chamber extends beyond said first end of said needle.

17. The apparatus according to claim 11, wherein the heat sealing device comprises:
   a first body having a first and second end, a bore extending therethrough, and a second aperture disposed perpendicular to said bore and adjacent said second end,
   a second body including a first and second end, a bore extending therethrough, and a second aperture disposed perpendicular to said bore, wherein said bore of the second body is adapted to receive said first body, and
   at least two heat sealing jaws disposed adjacent said second aperture, and tubing extending through said bore of said first body and said bore of said second body, and wherein said tubing is fixedly attached to said first end of said first body and said second body respectively.

18. The heat sealing device of claim 11, wherein the heat sealing device is disposed within the cabinet.

19. A method for removing a organic fluid from a patient, conditioning the organic fluid, and returning the organic fluid to the patient without contamination, the method comprising:
   removing the organic fluid from the patient;
   receiving the removed organic fluid in a container;
   conditioning the organic fluid in the container; and
   delivering the conditioned organic fluid to the patient by delivering the conditioned organic fluid from the container to a syringe comprising a plunger slidable within a tube, sealing a tube between the container and the syringe, and separating the syringe from the container;
   wherein contamination of the organic fluid, contamination of the conditioning apparatus, and contamination of the operator are prevented between removal of the organic fluid from the patient and delivery of the organic fluid back to the patient.

20. The method of claim 19, wherein the conditioned organic fluid is delivered to the patient by a double ended needle inserted in a portion of the tube remaining connected to the syringe after sealing.

21. The method of claim 19, wherein the sealing of the tube between the container and the syringe is performed by a heat sealing device.

* * * * *